US011075011B2

(12) United States Patent
Sanghvi et al.

(10) Patent No.: US 11,075,011 B2
(45) Date of Patent: Jul. 27, 2021

(54) DATA DRIVEN PREDICTIVE ANALYSIS OF COMPLEX DATA SETS FOR DETERMINING DECISION OUTCOMES

(71) Applicant: Grand Rounds, Inc., San Francisco, CA (US)

(72) Inventors: Jayodita Sanghvi, San Francisco, CA (US); Robert Sharp, San Francisco, CA (US); Nathaniel Freese, San Francisco, CA (US)

(73) Assignee: GRAND ROUNDS, INC., San Francisco, CA (US)

( * ) Notice: Subject to any disclaimer, the term of this patent is extended or adjusted under 35 U.S.C. 154(b) by 0 days.

(21) Appl. No.: 16/785,503

(22) Filed: Feb. 7, 2020

(65) Prior Publication Data
US 2020/0175007 A1 Jun. 4, 2020

Related U.S. Application Data

(63) Continuation of application No. 15/620,736, filed on Jun. 12, 2017, now Pat. No. 10,579,636, which is a
(Continued)

(51) Int. Cl.
*G06F 16/00* (2019.01)
*G16H 70/20* (2018.01)
*G06Q 30/02* (2012.01)
*G06F 16/248* (2019.01)
*G06F 16/242* (2019.01)
*G06F 16/2455* (2019.01)
*G06F 16/2457* (2019.01)
*G16H 50/70* (2018.01)
(Continued)

(52) U.S. Cl.
CPC .......... *G16H 70/20* (2018.01); *G06F 16/244* (2019.01); *G06F 16/248* (2019.01); *G06F 16/2455* (2019.01); *G06F 16/24575* (2019.01); *G06Q 30/0204* (2013.01); *G16H 10/60* (2018.01); *G16H 40/20* (2018.01); *G16H 50/20* (2018.01); *G16H 50/70* (2018.01)

(58) Field of Classification Search
CPC .................................................. G06F 16/248
See application file for complete search history.

(56) References Cited

U.S. PATENT DOCUMENTS

| 2006/0020580 A1 | 1/2006 | Dettinger et al. |
| 2007/0112889 A1 | 5/2007 | Cook et al. |
| 2015/0248537 A1 | 9/2015 | McClung et al. |

*Primary Examiner* — Ajith Jacob
(74) *Attorney, Agent, or Firm* — Finnegan, Henderson, Farabow, Garrett & Dunner, LLP

(57) ABSTRACT

Systems and methods are provided for data driven predictive analysis of complex data sets for determining decision outcomes. The systems and methods include obtaining a first set of data associated with individuals and obtaining, a second set of data associated with events, wherein the events are associated with at least one of the individuals. The systems and methods further include determining a subset of the individuals from the first set of data based on the first subset of individuals having common attributes with a target individual and determining a second subset of events from the second set of data based on the second subset of events having common attributes with the target events associated with the target individual. Additionally, the systems and methods include aggregating data associated with the second subset of events based on the target events and providing for display output associated with aggregated data.

20 Claims, 12 Drawing Sheets

Related U.S. Application Data continuation of application No. 15/269,888, filed on Sep. 19, 2016, now Pat. No. 9,679,028.

(51) Int. Cl.
*G16H 50/20* (2018.01)
*G16H 40/20* (2018.01)
*G16H 10/60* (2018.01)

| Person ID | Gender | Age | Location | Job Type |
|---|---|---|---|---|
| 1 | M | 54 | 20002 | Construction |
| 2 | M | 60 | 94403 | Engineering |
| 3 | F | 46 | 94301 | Service |
| 4 | F | 70 | 43081 | Management |
| 5 | M | 27 | 10001 | Accounting |
| . | . | . | . | . |
| . | . | . | . | . |
| . | . | . | . | . |
| N | M | 32 | 46556 | Military |

Fig. 4

| Event ID | Person ID | Cost | Code1 | Code2 | Code3 | Date | Professional ID |
|---|---|---|---|---|---|---|---|
| 1 | 1 | $8,000 | 409 | 10021 | R0076 | 1/1/2010 | 3 |
| 2 | 1 | $2,500 | 531 | 0001F | C9602 | 9/26/2012 | 3 |
| 3 | 1 | $100 | 461 | 47350 | A9152 | 7/27/2015 | 3 |
| 4 | 3 | $1,200 | 780.52 | 72345 | A9273 | 7/23/2005 | 3 |
| 5 | 5 | $180 | 787 | 99214 | G0009 | 3/17/2011 | 2 |
| 6 | 5 | $55 | 786.2 | 99213 | A4209 | 6/3/2013 | 5 |
| . | . | . | . | . | . | . | . |
| . | . | . | . | . | . | . | . |
| . | . | . | . | . | . | . | . |
| N | N | $150 | 523 | 97154 | G0205 | 2/5/2014 | 1 |

Fig. 5

| Event ID | Product ID | Person ID | Cost | Date | Professional ID |
|---|---|---|---|---|---|
| 1 | 0573-0133 | 1 | $4,500 | 1/1/2010 | 3 |
| 2 | 29485-1887 | 1 | $5,500 | 9/26/2012 | 3 |
| 3 | 30142-027 | 1 | $325 | 7/27/2015 | 3 |
| 4 | 30142-055 | 3 | $500 | 7/23/2005 | 3 |
| 5 | 64406-011 | 5 | $1,000 | 3/17/2011 | 2 |
| 6 | 66758-050 | 5 | $60 | 6/3/2013 | 7 |
| . | . | . | . | . | . |
| . | . | . | . | . | . |
| . | . | . | . | . | . |
| N | ZZ | N | $150 | 2/5/2014 | 18 |

Fig. 6

| Professional ID | Gender | Age | Location | Specialty | Affiliations |
|---|---|---|---|---|---|
| 1 | M | 54 | 94403 | Cardiology | PAMF |
| 2 | M | 60 | 92037 | Pediatrics | Scripps |
| 3 | F | 46 | 44195 | Orthopaedics | Cleveland Clinic |
| 4 | F | 70 | 85259 | Neurology | Mayo Clinic |
| 5 | M | 27 | 90048 | Internal Medicine | Cedar Sinai |
| . | . | . | . | . | . |
| . | . | . | . | . | . |
| . | . | . | . | . | . |
| N | M | 32 | 21287 | Ophthalmology | Johns Hopkins |

Fig. 7

| ••• | Event creator | Case analysis | Case savings |

Event creator

Event name
[ Surgery X ] — 902

Keyword tags
[ surgery x minimally invasive spine ]

Specialities          Regions of body
[ orthopedics ]           [ spine ]            — 903

Event type
◉ Procedure  ○ Diagnosis  ○ Drug

Procedure codes — 904
CPt/HCPCS code ▼   [ BETWEEN ▼ ]   [ 10000 ▼ ]   AND   [ 10005 ▼ ]   [ x Remove ]
ICD-9 procedure code ▼   [ IN ▼ ]   [ 10.00 ▼ ]                        [ x Remove ]
                                                                       [ + Add ]

Sources used — 905
[                    ]

Comments
[                    ]

[ Save ]

| Event creator | Case analysis | Case savings |

Case analysis

Case name

912 — Surgery X cancelled

Patient situation

Patient Inputs

Case ID

913 — 0123456789abcdef

Patient ID fedcba9876543210

Customer

[ ▼ ]

Completion date 2016-06-22

Indirect cost inputs

914 — Specialty

Orthopedics ▼

Ortho subspecialty

Spine ▼

Case type

Surgery/procedure cancelled ▼

Treatment path inputs

Fig. 9B

| Orthopedics ▼ | Spine ▼ | Surgery/procedure cancelled ▼ |

Treatment path inputs

| Path type | Path weight | Start date criteria | Other inclusion criteria | Exclusion criteria |
|---|---|---|---|---|
| Default ▼ | 1 ⊕ | | | x Remove |
| Expert ▼ | .5 ⊕ | | | x Remove |
| Expert ▼ | .5 ⊕ | | | x Remove |
| | | | | + Add |

Comments

Run full analysis

DATA DRIVEN PREDICTIVE ANALYSIS OF COMPLEX DATA SETS FOR DETERMINING DECISION OUTCOMES

REFERENCE TO RELATED APPLICATIONS

This application is a continuation of U.S. Non-Provisional patent application Ser. No. 15/620,736, filed on Jun. 12, 2017, now U.S. Pat. No. 9,679,028, which is a continuation of U.S. Non-Provisional patent application Ser. No. 15/269,888, filed on Sep. 19, 2016, the disclosure of which is expressly incorporated herein by reference in its entirety.

BACKGROUND

An ever increasing amount of data and data sources are now available to researchers, analysts, organizational entities, and others. This influx of information allows for sophisticated analysis but, at the same time, presents many new challenges for sifting through the available data and data sources to locate the most relevant and useful information. As the use of technology continues to increase, so, too, will the availability of new data sources and information.

Various methods can be used for analyzing data. Analytical or predictive models, one such method, provide a mechanism for evaluating the future result or outcome of multiple different choices or courses of action. Often these models are populated with speculative data that includes estimated probabilities or costs for predictive estimation. Current systems, however, do not provide sophisticated techniques for leveraging the vast amounts of available data to provide accurate data matching and more effective modeling.

BRIEF DESCRIPTION OF THE DRAWINGS

Reference will now be made to the accompanying drawings showing example embodiments of this disclosure. In the drawings:

FIG. 4 is an exemplary data structure, consistent with embodiments of the present disclosure.

FIG. 5 is an exemplary data structure, consistent with embodiments of the present disclosure.

FIG. 6 is an exemplary data structure, consistent with embodiments of the present disclosure.

FIG. 7 is an exemplary data structure, consistent with embodiments of the present disclosure.

FIGS. 9A-9C are exemplary interfaces, consistent with embodiments of the present disclosure.

DETAILED DESCRIPTION

Figure 1:
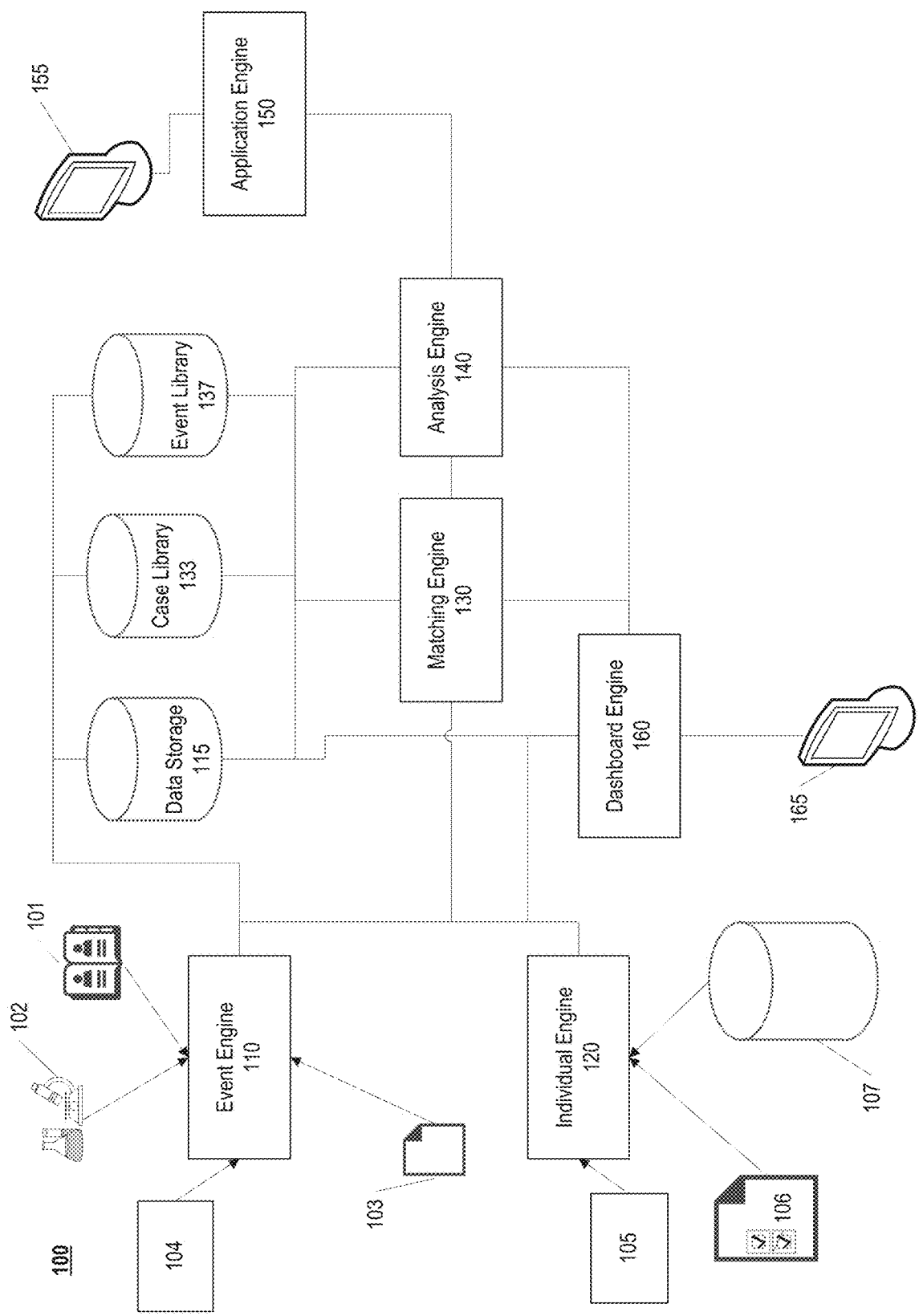
FIG. 1 is a block diagram of an exemplary system for data driven predictive analysis of complex data sets, consistent with embodiments of the present disclosure.

Reference will now be made in detail to the exemplary embodiments implemented according to the present disclosure, the examples of which are illustrated in the accompanying drawings. Wherever possible, the same reference numbers will be used throughout the drawings to refer to the same or like parts.

Predictive analysis can provide invaluable information for analyzing past performance and decisions. By analyzing past decisions, effective cost analysis can allow for organizations or entities to better evaluate past courses of action and performance, and identify ways to improve the decision making process.

This type of analysis can have benefits in many type of domains. The analysis can be extremely beneficial in the realm of healthcare. By analyzing the large amounts of claims data, prescription data, patient demographic data, and physician data that is available, accurate models can be built that can help analyze past healthcare decisions regarding patient care. Because the cost of patient procedures can be extremely high, and can vary across many factors, accurate methods of determining the effectiveness of past decisions is crucial. By having efficient and accurate methods of analyzing past data, organizations can analyze the effect of their recommendations on subsequent patient costs.

The systems and methods for analysis described herein can be used to match an existing patient who is considering one or more treatment options with past patients in similar circumstances. The system can analyze the large amounts of patient demographic information to find similarly situated individuals who underwent treatment for the condition. Combined with knowledge of which specific demographics, such as age, sex, past history, or other demographics, intelligent decisions can be made about which data should be included in the model. The data can then be analyzed to determine costs associated with the different treatment options that can be incurred over many months or years based on what has occurred in the past. This can result in better and more complete information for patients and help organizations evaluate the effectiveness of its recommendations.

Additionally, the system can provide information related to past treatment decisions. This can help insurance providers, hospitals, or others in the healthcare industry to analyze the past decision of physicians, clinics, or others in order to make determinations on the effect different recommendations may have on overall treatment costs. In doing so, insurance network providers or others using the system can ensure that they are adequately planning for potential costs associated with various treatments.

This type of analysis is made possible by utilizing known and empirical data. Instead of relying on theoretical data such as academic journals, which can make broad general conclusions based on small sample sets or speculative thinking, the system can utilize known values and data. Because of the amount of data available, the system can effectively target very specific data sets that are uniquely tailored to each individual patient. In doing so, each patient receives the absolute best recommendations the most effective and efficient treatment.

The embodiments described herein provide technologies and techniques for evaluating large numbers of data sources and vast amounts of data used in the creation of a predictive or analytical data model. The embodiments can include systems and methods for obtaining, from one or more data sources, a first set of data associated with a plurality of individuals; obtaining, from one or more data sources, a second set of data associated with a plurality of events, wherein the events are associated with at least one of the plurality of individuals; determining a first subset of one or more individuals from the first set of data based on a the first subset of one or more individuals having one or more common attributes with a target individual; determining a second subset of one or more events from the second set of data based on the second subset of one or more events having one or more common attributes with one or more target events associated with the target individual; aggregating data associated with the second subset of one or more events based on the one or more target events; and providing for display output associated with aggregated data.

Additional embodiments described herein include technologies and techniques wherein the one or more common attributes of the one or more events and the one or more target events are common attributes that are relevant, and wherein the relevancy of the one or more common attributes is based on the one or more target events.

The technologies and techniques described herein can further include aggregating the data from the second subset of one or more events by applying statistical operations to the data and generating a weight value associated with each of the target events.

In embodiments consistent with the present disclosure, the output can include a representation of the aggregation and a representation of the data used in the aggregation.

Additional embodiments include technologies and techniques wherein one or more attributes of the first set of data and one or more attributes of the second set of data are generated based on information from more than one data source.

The embodiments described herein can apply to many fields. Descriptions and applications related to specific domains do not preclude the application of the described embodiments to other technologies of fields.

FIG. 1 is a block diagram representing exemplary system 100 for data driven predictive analysis consistent with embodiments of the present disclosure. System 100 can utilize data sources 101-107. System 100 can further include event engine 110 and individual engine 120 for processing data sources 101-107. System 100 can additionally include matching engine 130, analysis engine 140, application engine 150, and dashboard engine 160. These components can be implemented using computing device 200, described in more detail below in reference to FIG. 2 and client device 300, described in more detail below in reference to FIG. 3. For example, data from data sources 101-107 can be obtained through I/O devices 230 and/or network interface 218 of computing device 200. System 100 can utilize data storage 115, case library 133, and event library 137 for storing various types of data. Data storage 115, case library 133, and event library 137 can be implemented using a suitable storage devices such as storage 228 and/or system memory 221 of device 200 described in FIG. 2. In some embodiments, data storage 115, case library 133, and event library 137 can be remote from computing device 200. System 100 can provide output on display 155 and 165. Display 155 and 165 can be display device 224 of FIG. 2 or display 406 of FIG. 3.

Each of event engine 110, individual engine 120, matching engine 130, analysis engine 140, application engine 150, and dashboard engine 160 can be a module, which is a packaged functional hardware unit designed for use with other components (e.g., portions of an integrated circuit) or a part of a program (stored on a computer readable medium) that performs a particular function of related functions. Each of these modules can be implemented using computing device 200 of FIG. 2. Each of these components is described in more detail below. In some embodiments, the functionality of system 100 can be split across multiple computing devices (e.g., multiple devices similar to computing device 200) to allow for distributed processing of the data. In these embodiments the different components can communicate over I/O device 230 or network interface 218 of FIG. 2's computing device 200.

System 100 can be related to many different domains or fields of use. Descriptions of embodiments related to specific domains, such as healthcare, is not intended to limit the disclosed embodiments to a those specific domains, and embodiments consistent with the present disclosure can apply to any domain that utilizes predictive modeling based on available data.

The data used by system 100 can originate from a variety of sources. The data sources can include publicly available information, proprietary analysis or data sources, and privately held information. For example, data sources can include claims data (e.g., claims 104), physician data (e.g., physicians 101), drug or prescription data (e.g., prescription data 102), and other event specific data (e.g., data 103). Moreover this data can come from a variety of sources including publicly accessible systems and internal databases or propriety information. Additional data sources can represent individual or patient data. for example, individual data can include patient demographic data (e.g., data source 106) and family history (e.g., data source 107). These examples are not exhaustive and other sources related to events can be used by system 100. It is appreciated that the above mentioned sources are exemplary. Any source of information (including either public or private information) that can be accessed and can provide relevant data, can contribute to the corpus of data available to system 100. The total number of sources can be smaller or larger than shown in FIG. 1.

Data can be provided to system 100 using a variety of data structures. For example, data structure 400, 500, 600, and 700 of FIGS. 4, 5, 6, and 7, described in more detail below, Data structure 400 can related to individuals and data structures 500, 600, and 700 can relate to event data.

As shown in FIG. 4, data structure 400 is an exemplary data structure, consistent with embodiments of the present disclosure. Data structure 400 can store data records associated with individuals or entities. Data structure 400 can, for example, be a database, a flat file, data stored in memory (e.g., system memory 221), and/or data stored in any other suitable storage mechanism (e.g., storage 228).

In some embodiments, data structure 400 can be a Relational Database Management System (RDBMS) (e.g., Oracle Database, Microsoft SQL Server, MySQL, PostgreSQL, and/or IBM DB2). An RDBMS can be designed to efficiently return data for an entire row, or record, in as few operations as possible. An RDBMS can store data by serializing each row of data of data structure 400. For example, in an RDBMS, data associated with record 401 of FIG. 4 can be stored serially such that data associated with all categories of record 401 can be accessed in one operation. Moreover, an RDBMS can efficiently allow access of related records stored in disparate tables. For example, in an RDBMS, data structure 400 of FIG. 4 and data structure 500 (described in more detail below) of FIG. 5 can be linked by a referential column. In this example, person ID 520 of data structure 500 can directly relate to person ID 410 of data structure 400. An RDBMS can allow for the efficient retrieval of all records in data structure 500 associated with a record of data structure 400 based on a common value for the respective person ID fields (e.g., person ID 520 of data structure 500 and person ID 410 of data structure 400).

In some embodiments, data structure 400 of FIG. 4 can be a non-relational database system (NRDBMS) (e.g., XML, Cassandra, CouchDB, MongoDB, Oracle NoSQL Database, FoundationDB, and/or Redis). A non-relational database system can store data using a variety of data structures such as, among others, a key-value store, a document store, a graph, and a tuple store. For example, a non-relational database using a document store could combine all of the data associated with a particular person ID (e.g., person ID 410 of data structure 400 and person ID 520 of data structure 500 in FIG. 5) into a single document encoded using XML. In this example, the XML document would include the information stored in record 410 of data structure 400 and records 501-503 of data structure 500 based on all of these records sharing the same person ID value.

Data structure 400 of FIG. 4 can store information related to individuals. Data structure 400 can include data records 401-405 representing individuals in addition to countless additional records up to record 499. Data structure 400 can contain many millions or billions of records of data and is limited only by the physical constraints of the system upon which the data structure exists.

Data structure 400 can include categories of data. For example data structure 400 can include categories person ID 410, gender 420, age 430, location 440, and job type 450. Data associated with data records 401-405 can be stored under each of these categories. For example, an individual represented by data record 401 has a person ID of "1," is male as represented by an "M" under gender 420, is 54 as listed under age 430, lives in zip code "20002" as represented under location 440, and works in construction as indicated under job type 450.

In some embodiments, data structure 400 can contain more or fewer categories for each data record. For example, data structure 400 can include additional categories of data such as household income, height, weight, eye color, hair color, race, education, or any other category of data associated with an individual. Moreover, depending on the circumstances data structure 400 can contain domain specific data. For example, in a healthcare context, data structure 400 can include insurance provider information, family medical history information, immunization information, or other healthcare specific data. Accordingly data structure 400 is not limited to only those categories shown in FIG. 4.

In some embodiments, data structure 400 contains categories that store similar data. For example, data structure 400 can include location 440 that represents a home address zip code, while an additional "location" category (not shown) can be used to store a business zip code.

Additionally, data structure 400 can include combination categories. For example, instead of only using location 440 to represent location information, data structure 400, in some embodiments, includes categories for, among others, street address, state, city, and/or country. This data can be stored under one category or separate categories that, together, represent a location.

Moreover, location 440 can store different types of data. In some embodiments, location 440 is a zip code. In other embodiments, location 440 is a combination category as previously described. Location 440 can further include, geospatial coordinates, map coordinates, or any other data type that indicates location.

Similarly to location 440, other categories, such as age 430 and job type 450, can include data in a variety of formats. For example, age 430 can be represented in years, in years and months, in days, or by a date of birth. Additionally, job type can be a specific job title, job classification, and/or industry.

In some embodiments, data stored under a category can be a reference into another data set or data structure as is common in relational data sets. For example, job type 450 can contain an identifier that references a description stored in a separate data set or lookup table instead of containing text or another data type.

Additionally, as shown in FIG. 5, data structure 500 is an exemplary data structure, consistent with embodiments of the present disclosure. Data structure 500 can store data records associated with events that are further associated with specific individuals. Similarly to data structure 400 described in FIG. 4, data structure 500 can, for example, be a database, a flat file, data stored in memory (e.g., system memory 221 of computing device 200 from FIG. 2), an RDBMS, an NRDBMS, and/or data stored in any other suitable storage mechanism (e.g., storage 228 of computing device 200 from FIG. 2). Moreover, data structure 500 can be implemented or stored computing device similar to computing device 200 described in FIG. 2.

Data structure 500 can store information related to events. Data structure 500 can include data records 501-506 representing data associated with specific events in addition to countless additional records up to record 599. Data structure 500 can contain millions or billions of records of data and is limited only by the physical constraints of the system upon which the data structure exists.

Data structure 500 can include categories of data. For example, data structure 500 can include the categories event ID 510, person ID 520, cost 530, code 1 540, code 2 550, code 3 560, date 570, and professional ID 580. Data associated with data records 501-506 can be stored in each respective row of data structure 500 within one of these categories. For example, an event represented by data record 501 is associated with a person ID 520 of "1," has a cost 530 of "$8000," has values of "409," "10021," and "R0076," for code 1 540, code 2 550, and code 3 560, respectively, a date 570 of "1/1/3010," and a professional ID 580 of "3."

Moreover, data structure 500 can include multiple data records associated with the same individual or professional. For example, data records 501-503 all have a value of 1 for person ID 520. Moreover, data records 501-504 all have a value of 3 for professional ID 580. These values can refer to a person ID number or professional ID number stored in a separate data set. For example, person ID 420 can refer to person ID 410 of data structure 400 described in FIG. 4. In this example, data records 501-503 of data structure 500 can be associated with data record 401 of data structure 400. Moreover, data record 503 of data structure 500 can be associated with data record 403 of data structure 400 and data records 505-506 of data structure 500 can be associated with data record 405 of data structure 400 based on the values in personal ID 520 and the values of personal ID 410 of data structure 400 in FIG. 4.

In some embodiments, the data records in data structure 500 are all related to the same type of event or a specific domain. For example, data structure 500 can contain data records related to medical insurance claims. In these embodiments, data structure 500 includes additional categories that are specific to these types of events or domains, such as categories for deductibles. Moreover, in these embodiments, existing categories may contain information related to the domain of the data. For example, in embodiments where data structure 500 includes health insurance claim data, code 1 540, code 2 550, and code 3 560 can represent International Statistical Classification of Diseases and Related Health Problems (ICD) codes, Current Procedural Terminology (CPT) codes, and Healthcare Common Procedure Coding System (HCPCS) codes respectively. Additionally, these types of codes can represent hierarchical data. Accordingly, a specific code in one of code 1 540, code 2 550, or code 3, 560 may imply additional codes or procedures based on the specific classification system in use. In a different domain, code 1 540, code 2 550, and code 3 560 can represent different identifying information for the events represented in data structure 500.

Similarly to data structure 400, data structure 500 can include more or fewer categories for each data record depending on the domain and the source of the data record. Additionally, as described in relation to data structure 400, some categories of data structure 500 can store data in different formats that represent the same concept, such as a date or cost. For example, date 570 can contain only a month and year, or can contain month, day, and year. In a similar example, cost can contain values in terms of United States Dollars or in terms of other currencies.

Additionally, as shown in FIG. 6, data structure 600 is an exemplary data structure, consistent with embodiments of the present disclosure. Data structure 600 can store data records associated with events that are further associated with specific individuals. Similarly to data structure 400 and data structure 500 described in FIGS. 4 and 5, data structure 600 can, for example, be a database, a flat file, data stored in memory (e.g., system memory 221 of computing device 200 from FIG. 2), an RDBMS, an NRDBMS, and/or data stored in any other suitable storage mechanism (e.g., storage 228 of computing device 200 from FIG. 2). Moreover, data structure 600 can be implemented or stored in a computing device similar to computing device 200 described in FIG. 2.

Data structure 600 can store information related to events associated with a product. For example, event could be the purchase of a product, or in the domain of healthcare, prescription information related to a drug. Data structure 600 can include data records 601-606 representing data associated with a specific event in addition to countless additional records up to record 699. Data structure 600 can contain millions or billions of records of data and is limited only by the physical constraints of the system upon which the data structure exists.

Data structure 600 can include categories of data. For example, data structure 600 can include the categories event ID 610, product ID 620, person ID 630, cost 640, date 650, and professional ID 660. Data associated with data records 601-606 can be stored in each respective row of data structure 600 within one of these categories. For example, an event represented by data record 601 is associated with a product ID 620 of "0573-0133," person ID 630 of "1," has a cost 640 of "$4,500," a date 650 of "Jan. 1, 2010," and a professional ID 680 of "5." In this example, product ID 620 can be a reference to the ID for a drug listing in the National Drug Code (NDC) database, and data record 601 can represent a prescription for a medication, such as Advil®. Moreover, data structure 600 can include multiple data records associated with the same individual or professional. For example, data records 601-603 all have a value of "1" for person ID 630. Moreover, data records 601-604 all have a value of 3 for professional ID 680. These values can refer to a person ID number or professional ID number stored in a separate data set. For example, professional ID 660 can refer to professional ID 710 of data structure 700 described below in more detail in reference to FIG. 7. In this example, data records 601-604 of data structure 600 can be associated with data record 703 of data structure 700. Moreover, data record 605 of data structure 600 can be associated with data record 702 of data structure 700 based on the values in professional ID 660 and professional ID 710 of data structure 700 in FIG. 7.

In some embodiments, the data records in data structure 600 are all related to the same type of event or a specific domain. For example, data structure 600 can contain data records related to drug prescription claims. In these embodiments, data structure 600 includes additional categories that are specific to these types of events or domains, such as categories for deductibles. Moreover, in these embodiments, existing categories may contain information related to the domain of the data. For example, in embodiments where data structure 600 includes drug prescription claim data, product ID 620 can represent National Drug Codes (NDC) that are part of the National Drug Code Directory.

Similarly to data structure 400 and data structure 500, data structure 600 can include more or fewer categories for each data record depending on the domain and the source of the data record. Additionally, as described in relation to data structures 400 and 500, some categories of data structure 600 can store data in different formats that represent the same concept, such as a date or cost. For example, date 650 can contain only a month and year, or can contain month, day, and year. In a similar example, cost can contain values in terms of United States Dollars or in terms of other currencies.

As shown in FIG. 7, data structure 700 is an exemplary data structure, consistent with embodiments of the present disclosure. Data structure 700 can store data records associated with professionals. While data structure 700 is shown to store information related to physicians, it is appreciated that it can store information related to any profession. Data structure 700 can, for example, be a database, a flat file, data stored in memory (e.g., system memory 221), and/or data stored in any other suitable storage mechanism (e.g., storage 228).

In some embodiments, data structure 700 can be a Relational Database Management System (RDBMS) (e.g., Oracle Database, Microsoft SQL Server, MySQL, PostgreSQL, and/or IBM DB2). An RDBMS can be designed to efficiently return data for an entire row, or record, in as few operations as possible. An RDBMS can store data by serializing each row of data of data structure 700. For example, in an RDBMS, data associated with record 701 of FIG. 7 can be stored serially such that data associated with all categories of record 701 can be accessed in one operation. Moreover, an RDBMS can efficiently allow access of related records stored in disparate tables. For example, in an RDBMS, data structure 700 of FIG. 7 and data structure 500 of FIG. 5 can be linked by a referential column. In this example, professional ID 580 of data structure 500 can directly relate to professional ID 710 of data structure 700. An RDBMS can allow for the efficient retrieval of all records in data structure 500 associated with a record of data structure 700 based on a common value for the respective professional ID fields (e.g., professional ID 580 of data structure 500 and professional ID 710 of data structure 700).

In some embodiments, data structure 700 of FIG. 7 can be a non-relational database system (NRDBMS) (e.g., XML, Cassandra, CouchDB, MongoDB, Oracle NoSQL Database, FoundationDB, and/or Redis). A non-relational database system can store data using a variety of data structures such as, among others, a key-value store, a document store, a graph, and a tuple store. For example, a non-relational database using a document store could combine all of the data associated with a particular professional ID (e.g., professional ID 710 of data structure 700 and professional ID 580 of data structure 500 in FIG. 5) into a single document encoded using XML. In this example, the XML document would include the information stored in record 702 of data structure 700 and record 505 of data structure 500 based on these records sharing the same professional ID value.

Data structure 700 of FIG. 7 can include data records 701-705 representing physicians in addition to countless additional records up to record 799. Data structure 700 can contain many thousands or millions of records of data and is limited only by the physical constraints of the system upon which the data structure exists.

Data structure 700 can include categories of data representing a physician. For example data structure 700 can include categories professional ID 710, gender 720, age 730, location 740, specialty 750, and affiliations 760. Data associated with data records 701-705 can be stored under each of these categories. For example, a physician represented by data record 701 has a person ID of "1," is male as represented by an "M" under gender 720, is 54 as listed under age 730, works in zip code "94403" as represented under location 740, specializes in cardiology as represented under specialty 750, and is affiliated with the Palo Alto Medical Foundation (PAMF) as represented by affiliations 760.

In some embodiments, data structure 700 can contain more or fewer categories for each data record. For example, data structure 700 can include additional categories of data such as certifications, education, publications, or any other category of data associated with a professional. Moreover, depending on the circumstances, data structure 700 can contain domain specific data. For example, in a healthcare context, in addition to healthcare specific specialty 750 and affiliations 760 data, data structure 700 can include insurance coverage information, practice or group name, teaching positions, or other information related to a physician. Accordingly data structure 700 is not limited to only those categories shown in FIG. 7.

In some embodiments, data structure 700 contains categories that store similar data. For example, data structure 700 can include location 740 that represents a home address zip code, while an additional "location" category (not shown) can be used to store a business zip code.

Additionally, data structure 700 can include combination categories. For example, instead of only using location 740 to represent location information, data structure 700, in some embodiments, includes categories for, among others, street address, state, city, and/or country. This data can be stored under one category or separate categories that, together, represent a location.

Moreover, location 740 can store different types of data. In some embodiments, location 740 is a zip code. In other embodiments, location 740 is a combination category as previously described. Location 740 can further include, geospatial coordinates, map coordinates, or any other data type that indicates location.

Similarly to location 740, other categories, such as age 730, specialty 750, and affiliations 760, can include data in a variety of formats. For example, age 730 can be represented in years, in years and months, in days, or by a date of birth.

In some embodiments, data stored under a category can be a reference into another data set or data structure as is common in relational data sets. For example, specialty 750 and affiliations 760 can contain an identifier that references a description stored in a separate data set or lookup table instead of containing text or another data type.

Referring back to FIG. 1, the data sources and the data provided by those sources can be dynamic. Data sources can continually be added, and data from those sources can be continually processed. As system 100 progresses, more data can be obtained and processed for later use.

Further, the data sources can be domain specific. Depending on the particular circumstances of system 100, certain types of data sources can be ignored or included. As an example, specific data sources for healthcare analysis can include, without limitation, administrative billing claims, third party vendors publishing average pricing benchmarks such as Healthcare Bluebook, Redbook, and PriceRX, published clinical studies or clinical trials, and health care practitioner (e.g., medical doctor) opinions and surveys.

Event engine 110 can process information related to event data and information from event data sources. Event engine 110 is a module, which is a packaged functional hardware unit designed for use with other components or a part of a program that performs a particular function of related functions. Event engine can process event information related to multiple individuals or can process information related to a specific individual. Event engine 110 can combine data from various data sources (e.g., data sources 101-104) in order to interpret the relevant data sources and data records. For example, event data such as claim data stored in data structure 500, prescription data stored in data structure 600, and physician data stored in data structure 700 can be correlated using the data fields available. As shown in reference to FIGS. 5, 6, and 7, data structure 500 and data structure 600 can include professional ID 660 that both reference professional ID 710 of data structure 700. By combining the information in the various data sources, event engine 110 can create treatment scenarios for various conditions.

In addition to combining data sources, event engine 110 can process multiple records in each individual data source. For example, a complex diagnosis can require multiple physician visits and multiple follow-up visits each represented as different records in claims data (e.g., multiple records in data structure 500). Additionally, multiple claim records can represent a duration of treatment. For example, multiple records spread over many months could represent medical claims for an ongoing treatment such as physical therapy. Depending on the specific codes used (e.g., code 1 540, code 550, and code 560 of data structure 500) event engine can 110 can determine the appropriate way to combine records and or data sources to represent specific courses of treatments or treatment paths.

Although, as described in relation to FIG. 5, claim data can reference standardized treatment codes, event engine 110 can utilize previously determined interpretations of treatment codes to provide a better categorization of individual codes or groups of codes. This previous analysis can be stored in proprietary databases or storage systems (e.g., data storage 115) and made available to event engine 110.

Similar to event engine 110, individual engine 120 is a module and can process various data sources providing information related a specific individual. Individual engine 120 can also combine data from various data sources (e.g., data sources 105-107) in order to interpret the relevant data sources and data records. For example, patient demographic data such as that stored in data structure 400 can be analyzed to provide additional context into a patient's history. Individual engine 120 can utilize single records from single data sources or combine various patient demographics and patient histories for a specific patient.

Moreover, the additional types of data, previously described, that can be generated based on data in various records stored in multiple data structures (e.g., data structures 400, 500, 600 or 700 can be stored in data storage 115. This generated data can be associated with particular individuals and events and can be stored as additional attributes on the stored data. Additionally, the various techniques, algorithms, or combinations of categories that are used to generate these attributes or data can also be stored in data storage 114.

In some embodiment, the output of event engine 110 and individual engine 120 can be stored (e.g., in data storage 115) for later use or processing. In some embodiments, the output of event engine 110 and individual engine 120 can be provided to dashboard engine 160. Dashboard engine, which is described in more detail below, can store the output of event engine 110 and individual engine 120 in case library 133 and/or event library 137. In particular, dashboard engine 160 can store the treatment paths associated with particular patient demographics in case library 133 as exemplary treatments for various specific patients. Additionally, dashboard engine 160 can be used to store specific medical and pharmaceutical events, such as, among others, diagnoses of symptoms or disorders, medical procedures, tests, surgeries, and prescription drug information. Costs can be associated with the various events and treatment paths can be associated with the events that occur as part of that specific treatment.

Additional events can also include indirect medical events that can have associated costs. For example, indirect costs can include productivity losses, missed work time, transportation or treatment costs, or any other subsequent event costs that, without the triggering event, would not be incurred.

System 100 can be provided with diagnosis and treatment options for a particular patient and the events that make up that treatment. System 100 can provide this information to matching engine 130. Matching engine 130 can compare the provided or target patient demographics and treatment options with other data available to the system to find past treatments that relate to the individual being analyzed.

In some embodiments, the output of event engine 110 and individual engine 120 can be provided to matching engine 130. In these embodiments, matching engine 130 can be used to prune the data provided to system 100 to allow for effective analysis of a specific patient. Matching engine 130 can analyze the large volume of information provided by event engine 110 and individual engine 120 as well as information stored in data storage 115, case library 133 to determine analyzed treatment paths related to a specific patient and diagnosis. Matching engine 130 can use a variety of factors to filter the data based on a specific treatment code. The matching or filtering can be based on specific treatment codes or be based on the clustering or analysis of treatment codes provided by event engine 110.

In addition to matching previously analyzed information to the target treatment options, matching engine 130 can also filter or match previously analyzed data based on the target patient demographics. For example, if the target patient is a senior citizen, matching engine 130 can disregard previously analyzed treatment data for patients who are not senior citizens. Matching engine 130 can further consider if the target demographics are relevant to the target treatment paths. For example, the age of the patient may not affect the efficacy or results of a particular treatment option. In these examples, the age can be ignored when matching engine 130 analyzes treatment options for the target patient.

In this way, matching engine 130 can utilize various sets of inclusion criteria and exclusion criteria for matching particular treatment paths. Inclusion criteria can be used to include the treatment paths for characteristics matching those of the target patient. Conversely, exclusion criteria can be used to exclude treatment paths based on the criteria that might otherwise be identified by matching engine 130 as a potential path for analysis. Inclusion and exclusions criteria can be related to the demographics or characteristics of the target patient and/or can be based on events stored in event library.

Matching engine 130 can utilize raw data stored in, for example, data storage 115. Additionally, matching engine 130 can utilize past treatment paths that have been analyzed and stored in case library 133 and medical event information stored in event library 137. Case library 133 can store treatment paths that are linked to specific patients. Accordingly, case library 133 can include treatment paths for the same condition or treatment options as other individuals who have been treated for the same condition or utilized the same treatment options as the target condition or treatment options.

Because each individual patient can have different experiences, complications, subsequent treatments, and other resulting events following a specific treatment, each individual's treatment paths can result in different events and costs. In some embodiments, many patients will have the same or very similar treatment paths for a specific condition or treatment. In addition to storing the specific treatments that occur on each individual's treatment path, case library 133 can store the cost associated with each treatment path and case library 137 can store cost information and other information related to events on the particular treatment path. In this way, case library 133 can store a large number of analyzed treatment paths for a target treatment that can be filtered by matching engine 130 based on criteria or settings specific to target patient and target treatment options.

In some embodiments, matching engine 130 can further filter the chosen treatment paths based on a severity score for the target patient. In these embodiments, the patient can be assigned a severity score to represent the particular severity of the patient's condition. The severity calculation can include factors such as, among others, age, gender, comorbidities, past costs, and geography. Matching engine 130 can select the set of treatment paths to provide an even distribution of patient severities and to closely approximate the target patients own severity score.

After matching engine 130 retrieves the relevant treatment paths and information from data storage 115, case library 133, and case library 137, matching engine 130 can provide the data to analysis engine 140. In some embodiments, analysis engine 140 can receive all of the data from matching engine 130. In other embodiments, analysis engine 140 can also access data in data storage 115, case library 133, and event library 137.

Analysis engine can use the data provided by matching engine 130, as well as data stored in data storage 115, case library 133, and event library 137 to calculate overall costs for each of the treatment paths provided. These treatment paths can be related to a single target treatment or can be related to multiple possible target treatment options for a specific patient. The cost associated with each potential target treatment option can be calculated by aggregating the treatment paths associated with each target treatment option.

Figure 8:
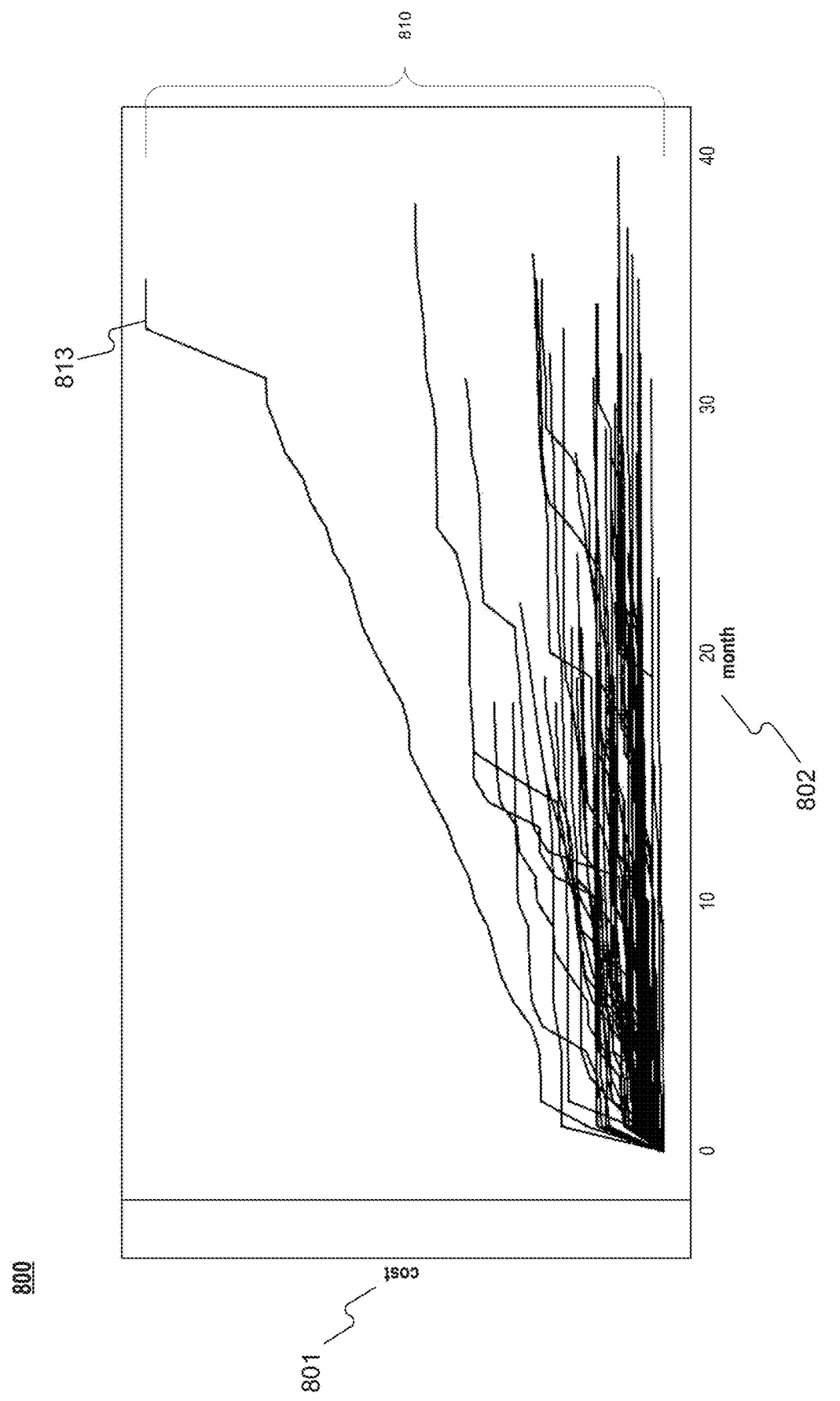
FIG. 8 is an exemplary analytical model, consistent with embodiments of the present disclosure.

FIG. 8 is a representation of an exemplary analytic model 800 consistent with embodiments of the present disclosure. Analytical model 800 can represent the analysis of treatment paths associated with a specified condition or treatment. Analytical model 800 can present the analyzed data in a visual manner to allow for easier analysis and interpretation of the data. Analytical model 800 can represent the cost 801 associated with each treatment path over time (e.g., month 802). For example, analytical model 800 can show the change in cost 801 of each treatment path analyzed as time progresses. Events along each treatment path causing an increase in cost can be represented by the increase in the line representing each treatment path.

The y axis of analytical model 800 can represent cost 801. Cost 801 can be scaled based on the available data or can represent a constant scale. Moreover, cost 801 can utilize a linear, logarithmic, or other type of scale to represent the cost associated with each treatment path. The x axis of analytical model 800 can represent the passage of time (e.g., month 802). The scale can be measured in days, months, years, or any other suitable time values.

For every treatment path analyzed, analytical model can include one or more paths 810 representing the cost of that specific treatment path over time. For example, path 813 can represent the most expensive treatment path analyzed. At month 802 0, the cost associated with path 813 can also be 0. As time increases, so does the height of path 813 to represent increasing cost over time. The specific values used for the cost at any given time can be dependent on the events that are associated with that particular treatment path. In some embodiments, if data is not available for the full time scale shown, analytical model 800 can extrapolate based on past data to predict future costs. Different methods of extrapolation are possible, such as utilizing an exponential decay curve to predict future costs.

After analyzing all identified treatment paths, analytical model 800 can provide the average cost associated with all of the analyzed treatments. Additional metrics can be used depending on the specific domain and purpose of analytical model 800.

Referring back to FIG. 1, analysis engine 140 can process the data, such as the data represented by analytical model 800, to determine the predicted cost associated with each target treatment option. In some embodiments, the cost associated with a particular target treatment option can be calculated by averaging each relevant treatment path that can result from choosing that option. Using an average can account for both variances in cost as well as variances in the frequency distribution of subsequent events and/or complications. By using a data driven approach to the analysis, the natural distribution of the data can help smooth outliers that might otherwise affect predicted costs for a particular treatment option.

After analyzing each treatment option, analysis engine can provide the results of the analysis and predicted cost for the different target treatment options to other components of system 100. The output can be provided to application engine 150 and can also be provided to dashboard engine 160.

Application engine 150 can process the output from analysis engine 140 (e.g., the data underlying analytical model 800) and provide a visual representation of the data. For example, a visual representation of the data can be similar to the representation of analytical model 800 in FIG. 8. Other representations can include a chart, a raw data display, or a textual description that can include the analytical model, treatment options, and/or predicted costs. The visual representation of the graph can be provided to display 155. Display 155 can be, for example, display device 224 of device 200, described below in reference to FIG. 2, or display 306 of client device 300 described below in reference to FIG. 3. In some embodiments, both application engine 150 and display 155 are part of the same device (e.g., device 200 of FIG. 2 or client device 300 of FIG. 3). In these embodiments, application engine 150 can directly connect to system 100 or can be connected to system 100 over a network or other communication systems. This connection can be provided by, for example, network interface 218 or I/O devices 230 of FIG. 2 and communications subsystem 304, short-range wireless communications 326, and data port 318 of FIG. 3. In other embodiments, system 100 can include application engine 150, and application engine 150 can provide a visual representation to display 155 using a network or some other communication link. Moreover, display 155, or components connected to display 155, can accept user input and provide that input to application engine 150. For example, user input can be captured by I/O devices 230 or network interface 218 of device 200 in FIG. 2 or input devices 308, short-range wireless communications 326, and communications subsystem 304 of client device 300 in FIG. 3. The output from application engine 150 can be utilized by a user of system 100 to analyze potential future costs as well as analysis of the potential or past costs for other treatment paths that were not chosen.

Dashboard engine 160 can process the output from analysis engine 140 (e.g., the data underlying analytical model 800) and provide a visual representation of the data. The representation can be the same as that provided by application engine 150 and display 155. The visual representation from dashboard engine 160 can be provided to display 165. Display 165 can be, for example, display device 224 of device 200, described below in reference to FIG. 2, or display 306 of client device 300 described below in reference to FIG. 3. In some embodiments, both dashboard engine 160 and display 165 are part of the same device (e.g., device 200 of FIG. 2 or client device 300 of FIG. 3). In these embodiments, dashboard engine 160 can directly connect to system 100 or can be connected to system 100 over a network or other communication systems. This connection can be provided by, for example, network interface 218 or I/O devices 230 of FIG. 2 and communications subsystem 304, short-range wireless communications 326, and data port 318 of FIG. 3. In other embodiments, system 100 can include dashboard engine 160, and dashboard engine 160 can provide a visual representation to display 165 using a network or some other communication link. Moreover, display 165, or components connected to display 165, can accept user input and provide that input to dashboard engine 160. For example, user input can be captured by I/O devices 230 or network interface 218 of device 200 in FIG. 2 or input devices 308, short-range wireless communications 326, and communications subsystem 304 of client device 300 in FIG. 3.

Additionally, dashboard engine 160 can provide an interface for interacting with other components of system 100. For example, dashboard engine 160 can provide a representation of data output by event engine 110 and individual engine 120. Additionally, dashboard engine 160 can provide representations of how the output from event engine 110 and individual engine 120 are eventually stored in case library 133 and event library 137. Dashboard engine 160 can be used to modify, update, or view the various data stored in case library 133 and event library 137. Through dashboard 160, a user or operator of system 100 can adjust (e.g., through an interface like that shown in FIGS. 9A-9C described in more detail below) the settings of the various components in order to improve the resulting predictions or the various operation of each individual component. The output from and interaction with dashboard engine 160 can occur through display 165.

FIGS. 9A-9C are exemplary interfaces 900 and 910, consistent with embodiments of the present disclosure. In some embodiments, interfaces 900 and 910 can be used to interact with system 100.

FIG. 9A is an exemplary interface 900, consistent with embodiments of the present disclosure. Interface 900 can be used to create events that can be stored in event library 137 of FIG. 1. The name of an event can be entered in name field 902. Additional keywords and other characteristics of the event can be entered in fields 903. These characteristics can include, among other things, keywords, specialties, regions of the body, and type of event (e.g., procedure, diagnosis, and/or pharmaceutical). Specific procedure codes for the event can be entered in code fields 904. Procedure codes can include, among other things, ICD codes, CPT codes, NDC codes, and brand drug names or generic drug names. Additional information about the source of the event and additional comments can be entered in fields 905.

FIGS. 9B-9C are exemplary embodiments of interface 910, consistent with embodiments of the present disclosure. Interface 910 can provide an access to case analysis on system 100 of FIG. 1. A case name can be entered in case name field 912. Additional patient information can be added using patient inputs 913. Indirect costs associated with the case can be included in indirect cost inputs 914. Additional inputs, shown in FIG. 9C, can be added to the case analysis. FIG. 9C, can be a continuation of interface 910 shown in FIG. 9B. Treatment path fields 915 can be used to input events that occurred in the specific case. Each event added using treatment path fields 915 can be events created using interface 900 shown in FIG. 9A and/or events stored in event library 137. The events entered using treatment path fields 915 can include inclusion and exclusion parameters associated with the events for the specific case.

Figure 2:
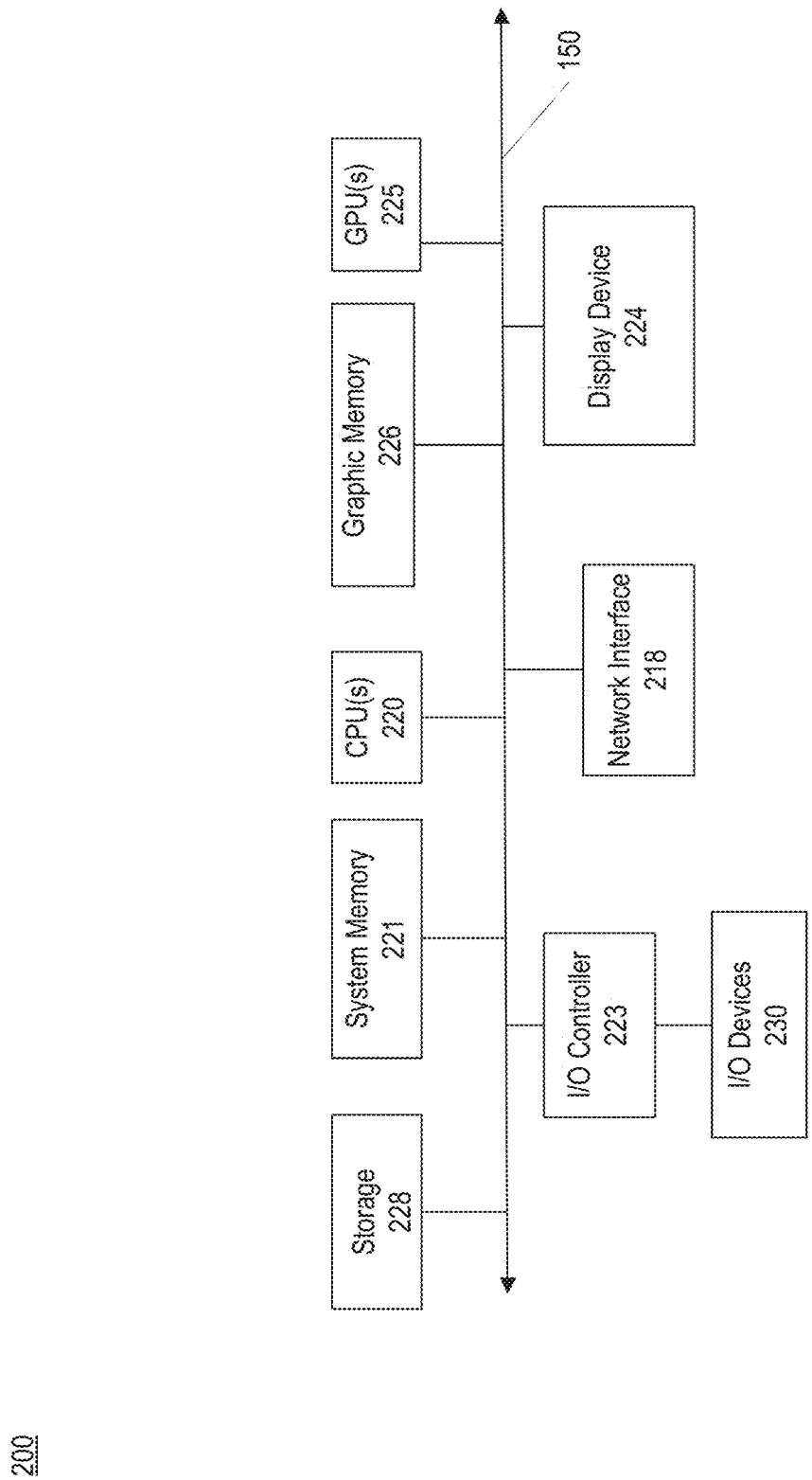
FIG. 2 is a block diagram of an exemplary computing device, consistent with embodiments of the present disclosure.

FIG. 2 is a block diagram of an exemplary computing device 200, consistent with embodiments of the present disclosure. In some embodiments, computing device 200 can be a specialized server providing the functionality described herein. In some embodiments, system 100 is implemented using computing device 200 or multiple computing devices 200 operating in parallel. Further, computing device 200 can be a second device providing the functionality described herein or receiving information from a server to provide at least some of that information for display. Moreover, computing device 200 can be an additional device or devices that store and/or provide data consistent with embodiments of the present disclosure. \

Computing device 200 can include one or more central processing units (CPUs) 220 and system memory 221. Computing device 200 can also include one or more graphics processing units (GPUs) 225 and graphic memory 226. CPUs 220 can be single or multiple microprocessors, field-programmable gate arrays, or digital signal processors capable of executing sets of instructions stored in a memory (e.g., system memory 221), a cache, or a register. CPUs 220 can contain one or more registers for storing variable types of data including, inter alia, data, instructions, floating point values, conditional values, memory addresses for locations in memory (e.g., system memory 221 or graphic memory 226), pointers and counters. CPU registers can include special purpose registers used to store data associated with executing instructions such as an instruction pointer, instruction counter, and/or memory stack pointer. System memory 221 can include a tangible and/or non-transitory computer-readable medium, such as a flexible disk, a hard disk, a compact disk read-only memory (CD-ROM), magneto-optical (MO) drive, digital versatile disk random-access memory (DVD-RAM), a solid-state disk (SSD), a flash drive and/or flash memory, processor cache, memory register, or a semiconductor memory. System memory 221 can be one or more memory chips capable of storing data and allowing direct access by CPUs 220. System memory 221 can be any type of random access memory (RAM), or other available memory chip capable of operating as described herein.

CPUs 220 can communicate with system memory 221 via a system interface 250, sometimes referred to as a bus. GPUs 225 can be any type of specialized circuitry that can manipulate and alter memory (e.g., graphic memory 226) to provide and/or accelerate the creation of images. GPUs 225 can store images in a frame buffer for output to a display device such as display device 224. GPUs 225 can have a highly parallel structure optimized for processing large, parallel blocks of graphical data more efficiently than general purpose CPUs 220. Furthermore, the functionality of GPUs 225 can be included in a chipset of a special purpose processing unit or a co-processor.

CPUs 220 can execute programming instructions stored in system memory 221 or other memory, operate on data stored in memory (e.g., system memory 221) and communicate with GPUs 225 through the system interface 250, which bridges communication between the various components of computing device 200. In some embodiments, CPUs 220, GPUs 225, system interface 250, or any combination thereof, are integrated into a single chipset or processing unit. GPUs 225 can execute sets of instructions stored in memory (e.g., system memory 221), to manipulate graphical data stored in system memory 221 or graphic memory 226. For example, CPUs 220 can provide instructions to GPUs 225, and GPUs 225 can process the instructions to render graphics data stored in the graphic memory 226. Graphic memory 226 can be any memory space accessible by GPUs 225, including local memory, system memory, on-chip memories, and hard disk. GPUs 225 can enable displaying of graphical data stored in graphic memory 226 on display device 224.

Computing device 200 can include display device 224 and input/output (I/O) devices 230 (e.g., a keyboard, a mouse, or a pointing device) connected to I/O controller 223. I/O controller 223 can communicate with the other components of computing device 200 via system interface 250. It is appreciated that CPUs 220 can also communicate with system memory 221 and other devices in manners other than through system interface 250, such as through serial communication or direct point-to-point communication. Similarly, GPUs 225 can communicate with graphic memory 226 and other devices in ways other than system interface 250. In addition to receiving input, CPUs 220 can provide output via I/O devices 230 (e.g., through a printer, speakers, or other output devices).

Furthermore, computing device 200 can include a network interface 218 to interface to a LAN, WAN, MAN, or the Internet through a variety of connections including, but not limited to, standard telephone lines, LAN or WAN links (e.g., 802.21, T1, T3, 56 kb, X.25), broadband connections (e.g., ISDN, Frame Relay, ATM), wireless connections, or some combination of any or all of the above. Network interface 218 can comprise a built-in network adapter, network interface card, PCMCIA network card, card bus network adapter, wireless network adapter, USB network adapter, modem or any other device suitable for interfacing computing device 200 to any type of network capable of communication and performing the operations described herein.

Figure 3:
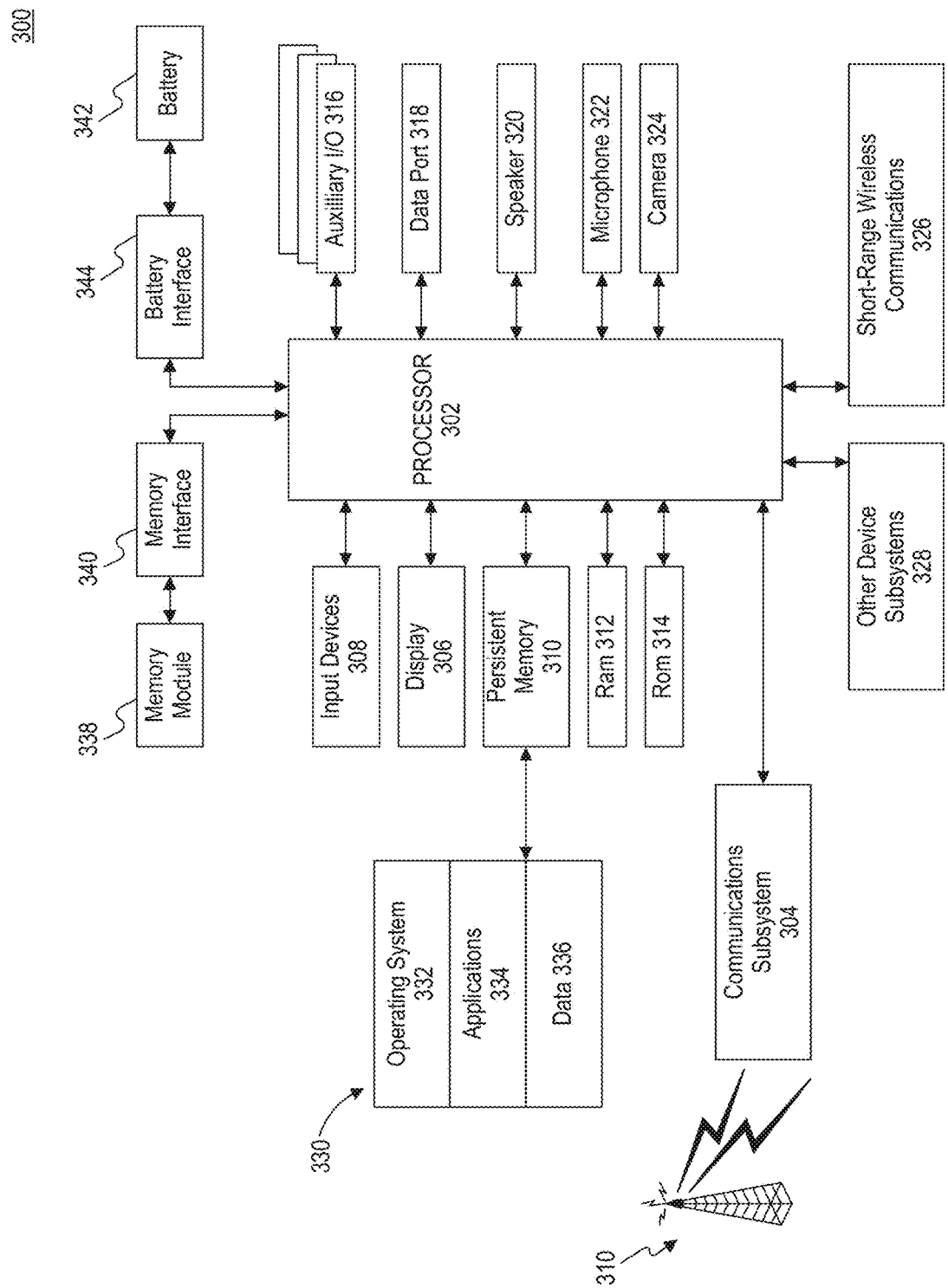
FIG. 3 is a block diagram of an exemplary computing device, consistent with embodiments of the present disclosure.

FIG. 3 is a simplified block diagram illustrating an example electronic device 300. In some embodiments, electronic device 300 can include a communication device having two-way or one-to-many data communication capabilities, audio communication capabilities, and/or video communication capabilities, and the capability to communicate with other computer systems, for example, via the Internet. Depending on the functionality provided by electronic device 300, in various embodiments, electronic device 300 can be a handheld device, a multiple-mode communication device configured for both data and voice communication, a smartphone, a mobile telephone, a laptop, a computer wired to the network, a netbook, a gaming console, a tablet, a smart watch, or a PDA enabled for wireless communication.

Electronic device 300 can include a case (not shown) housing component of electronic device 300. The internal components of electronic device 300 can, for example, be constructed on a printed circuit board (PCB). The description of electronic device 300 herein mentions a number of specific components and subsystems. Although these components and subsystems can be realized as discrete elements, the functions of the components and subsystems can also be realized by integrating, combining, or packaging one or more elements in any suitable fashion.

Electronic device 300 can include a controller comprising at least one processor 302 (such as a microprocessor), which controls the overall operation of electronic device 300. Processor 302 can be one or more microprocessors, field programmable gate arrays (FPGAs), digital signal processors (DSPs), or any combination thereof capable of executing particular sets of instructions. Processor 302 can interact with device subsystems such as a communication subsystem 304 for exchanging radio frequency signals with a wireless network to perform communication functions.

Processor 302 can also interact with additional device subsystems including a communication subsystem 304, a display 306 (e.g., a liquid crystal display (LCD) screen, a touch-screen display, or any other appropriate display), input devices 308 (e.g., a keyboard, a stylus, or control buttons), a persistent memory 310, a random access memory (RAM) 312, a read only memory (ROM) 314, auxiliary input/output (I/O) subsystems 316, a data port 318 (e.g., a conventional serial data port, a Universal Serial Bus (USB) data port, a 30-pin data port, a Lightning data port, or a High-Definition Multimedia Interface (HDMI) data port), a speaker 320, a microphone 322, camera 324, a short-range wireless communications subsystem 326 (which can employ any appropriate wireless (e.g., RF), optical, or other short range communications technology (for example, Bluetooth or NFC)), and other device subsystems generally designated as 328. Some of the subsystems shown in FIG. 3 perform communication-related functions, whereas other subsystems can provide "resident" or on-device functions.

Communication subsystem 304 includes one or more communication systems for communicating with a network and any external devices (e.g., a server, not shown). The particular design of communication subsystem 304 depends on the wireless network in which electronic device 300 is intended to operate. Electronic device 300 can send and receive communication signals over the wireless network after the required network registration or activation procedures have been completed.

In some embodiments, display 306 can be a touch-screen display. The touch-screen display can be constructed using a touch-sensitive input surface, which is coupled to an electronic controller and which overlays the visible element of display 306. The touch-sensitive overlay and the electronic controller provide a touch-sensitive input device and processor 302 interacts with the touch-sensitive overlay via the electronic controller.

Camera 324 can be a CMOS camera, a CCD camera, or any other type of camera capable of capturing and outputting compressed or uncompressed image data such as still images or video image data. In some embodiments electronic device 300 can include more than one camera, allowing the user to switch, during a video conference call, from one camera to another, or to overlay image data captured by one camera on top of image data captured by another camera. Image data output from camera 324 can be stored in, for example, an image buffer, which can be a temporary buffer residing in RAM 312, or a permanent buffer residing in ROM 314 or persistent memory 310. The image buffer can be, for example, a first-in first-out (FIFO) buffer.

Short-range wireless communications subsystem 326 is an additional optional component that provides for communication between electronic device 300 and different systems or devices, which need not necessarily be similar devices. For example, short-range wireless communications subsystem 326 can include an infrared device and associated circuits and components, or a wireless bus protocol compliant communication device such as a Bluetooth® communication module to provide for communication with similarly-enabled systems and devices.

Processor 302 can be one or more processors that operate under stored program control and executes software modules 330 stored in a tangibly-embodied non-transitory computer-readable storage medium such as persistent memory 310, which can be a register memory, a processor cache, a Random Access Memory (RAM), a flexible disk, a hard disk, a CD-ROM (compact disk-read only memory), and MO (magneto-optical), a DVD-ROM (digital versatile disk-read only memory), a DVD RAM (digital versatile disk-random access memory), or other semiconductor memories.

Software modules 330 can also be stored in a computer-readable storage medium such as ROM 314, or any appropriate persistent memory technology, including EEPROM, EAROM, FLASH. These computer-readable storage mediums store computer-readable instructions for execution by processor 302 to perform a variety of functions on electronic device 300. Alternatively, functions and methods can also be implemented in hardware components or combinations of hardware and software such as, for example, ASICs and/or special purpose computers.

Software modules 330 can include operating system software 332, used to control operation of electronic device 300. Additionally, software modules 330 can include software applications 334 for providing additional functionality to electronic device 300. For example, software applications 334 can include applications designed to interface with systems like system 100 above (e.g., software applications 334 can include implementations of application engine 150 and dashboard engine 160 described above in reference to FIG. 1).

Software applications 334 can also include a range of applications, including, for example, an Internet browser application, a voice communication (i.e., telephony or Voice over Internet Protocol (VoIP)) application, a media player application, a health-related application, a benefits-related application, etc. Each of software applications 334 can include layout information defining the placement of particular fields and graphic elements (for example, text fields, input fields, icons, etc.) in the user interface according to that corresponding application.

Operating system software 332 can provide a number of application protocol interfaces (APIs) providing an interface for communicating between the various subsystems and services of electronic device 300, and software applications 334. For example, operating system software 332 provides a user interface API to any application that needs to create user interfaces for display on electronic device 300. Accessing the user interface API can provide the application with the functionality to create and manage screen windows and user interface controls, such as text boxes, buttons, and scrollbars; receive mouse and keyboard input; and other functionality intended for display on display 306. Furthermore, a camera service API can allow a video communication application to access camera 324 for purposes of capturing image data.

In some embodiments, persistent memory 310 stores data 336, including data specific to a user of electronic device 300, such as information of user accounts. Persistent memory 310 can also store data obtained from network services or search results. Persistent memory 310 can further store data relating to various applications with preferences of the particular user of, for example, electronic device 300. In some embodiments, persistent memory 310 can store data 336 linking a user's data with a particular field of data in an application, such as for automatically entering a user's name into a username textbox on an application executing on electronic device 300. Furthermore, in various embodiments, data 336 can also include service data comprising information required by electronic device 300 to establish and maintain communication with a network.

In some embodiments, auxiliary input/output (I/O) subsystems 316 comprise an external communication link or interface, for example, an Ethernet connection. In some embodiments, auxiliary I/O subsystems 316 can further comprise one or more input devices, including a pointing or navigational tool such as a stylus, a clickable trackball or scroll wheel or thumbwheel, or a human finger; and one or more output devices, including a mechanical transducer such as a vibrator for providing vibratory notifications in response to various events on electronic device 300 (for example, receipt of a notification or a message or an incoming phone call), or for other purposes such as haptic feedback (touch feedback); or any combination thereof.

In some embodiments, electronic device 300 can also include one or more removable memory modules 338 (e.g., FLASH memory) and a memory interface 340. Removable memory module 338 can store information used to identify or authenticate a user or the user's account to a wireless network. For example, in conjunction with certain types of wireless networks, including GSM and successor networks, removable memory module 338 is referred to as a Subscriber Identity Module (SIM). Memory module 338 can be inserted in or coupled to memory module interface 340 of electronic device 300 in order to operate in conjunction with the wireless network.

Electronic device 300 can also include a battery 342, which furnishes energy for operating electronic device 300. Battery 342 can be coupled to the electrical circuitry of electronic device 300 through a battery interface 344, which can manage such functions as charging battery 342 from an external power source (not shown) and the distribution of energy to various loads within or coupled to electronic device 300.

A set of applications that control basic device operations, including data and possibly voice communication applications, can be installed on electronic device 300 during or after manufacture. Additional applications or upgrades to operating system software 332 or software applications 334 can also be loaded onto electronic device 300 through a wireless network, auxiliary I/O subsystem 316, data port 318, short-range wireless communication subsystem 326, or other suitable subsystem such as 328. The downloaded programs or code modules can be permanently installed, for example, written into the persistent memory 310, or written into and executed from RAM 312 for execution by processor 302 at runtime.

Electronic device 300 can provide three principal modes of communication: a data communication mode, a voice communication mode, and a video communication mode. In the data communication mode, a received data signal such as a text message, an e-mail message, Web page download, VoIP data, or an image file are processed by communication subsystem 304 and input to processor 302 for further processing. For example, a downloaded Web page can be further processed by a browser application, or data obtained from network connected applications or services can be processed and output to display 306. A user of electronic device 300 can also compose data items, such as contents for network based services, e-mail messages, for example, using the input devices, such as auxiliary I/O subsystem 316, in conjunction with display 306. These composed items can be transmitted through communication subsystem 304 over a wireless network. In the voice communication mode, electronic device 300 provides telephony functions and operates as a typical cellular phone. In the video communication mode, electronic device 300 provides video telephony functions and operates as a video teleconference terminal. In the video communication mode, electronic device 300 utilizes one or more cameras (such as camera 324) to capture video for the video teleconference.

Figure 10:
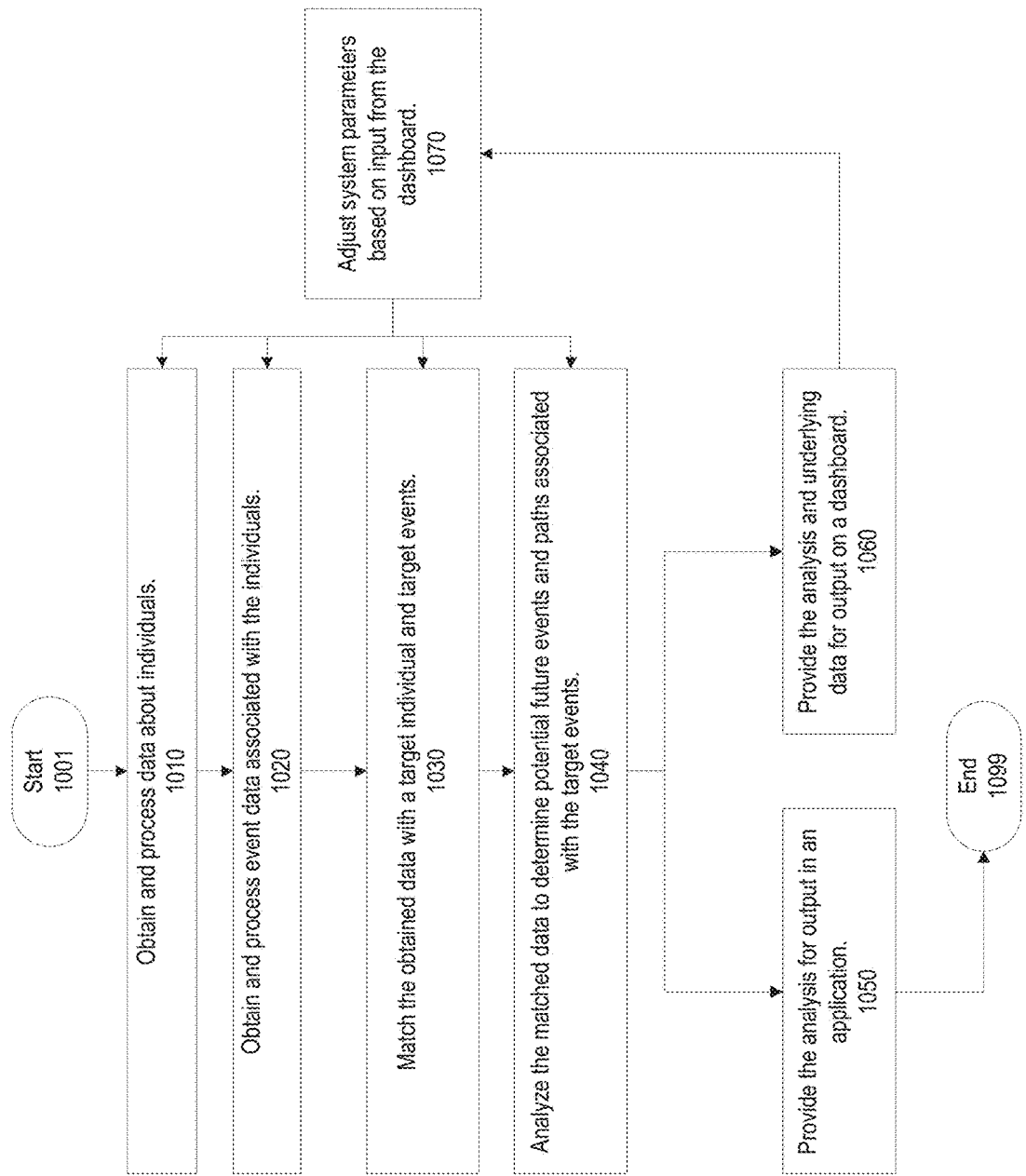
FIG. 10 is a flowchart of an exemplary method for data driven predictive analysis of complex data sets, consistent with embodiments of the present disclosure.

FIG. 10 is a flowchart of an exemplary method 1000 for data driven predictive analysis, consistent with embodiments of the present disclosure. It will be readily appreciated that the illustrated procedure can be altered to delete steps or further include additional steps. It is appreciated that one or more computing devices (such as computing device of FIG. 2) can perform the exemplary method and that the functionality described herein can be incorporated as hardware, software stored in the one or more computing devices, or any combination thereof. Moreover, the illustrated procedure can be applied to many different domains and descriptions related to a healthcare context are not intended to limit the disclosure to only that domain.

After initial step 1001, the system (e.g., system 100 from FIG. 1) can obtain and process (step 1010) data associated with individuals (e.g., in a healthcare context, patient data stored in data structure 400 of FIG. 4). Obtaining and processing the data can include, as described in relation to FIG. 1, processing data from multiple data sources (e.g., data sources 105-104, aggregating or interpreting the data, and storing the processed data into a storage location (e.g., data storage 115) for additional analysis. Through this process, the system can prepare data from a variety of sources into a normalized and consistent representation ready for further processing.

The system can further obtain and process (step 1020) event data (e.g., in a healthcare context, claims data, prescription drug data, and physician data store in data structures 500, 600 and 700 of FIGS. 5, 6, and 700) as described in relation to FIG. 1. Obtaining and processing the data can include processing data from multiple data sources (e.g., data sources 105-107), aggregating or interpreting the data, and storing the processed data into a storage location (e.g., data storage 115) for additional analysis. Through this process, the system can prepare data from a variety of sources into a normalized and consistent representation ready for further processing.

The system can match (step 1030) the event and individual data with previously processed data to obtain data relevant to predefined events or outcomes (e.g., using matching engine 130). The matching process can take into account an individual's demographic information and specific claim information to determine what criteria are appropriate for matching a specific individual and event paths. For example, in a healthcare context, the matching process can examine a target event and target treatment options and determine what if any demographic information is relevant. In some embodiments, demographic information, such as age, will be relevant and will affect the matched data. For example, certain types of surgery may be appropriate for a middle-aged person, while inappropriate for children or the elderly. Each type of demographic information can be weighted accordingly based on its relevance to the target event and/or target treatment options. Conversely, in some embodiments the age of the patient is irrelevant and the matched data can ignore any age considerations. The matching step can output treatment path information that relates to the target event and target treatment options. Using the target individual and target event to compare against the event data can make the processing of the relevant data more efficient, thereby saving system resources. By identifying specific treatment paths that can be removed because of differences in demographic attributes from the target patient, the system can eliminate inefficiency and inaccuracy that is introduced by processing extraneous or irrelevant data.

The system can further analyze (step 1040) the matched data. The system can utilize analytic methods such as graphs (e.g., analytical model 800 of FIG. 8) to interpret the matched data. The system can determine all matched treatment paths that flow from the various target treatment options and use the underlying data to calculate the cost associated with each individual treatment path. The system can combine or aggregate the cost data that stems from a particular target treatment option by, for example, averaging the cost of each individual treatment path that represents the target treatment path.

The system can provide (step 1050) the results of the analysis for display (e.g., using application engine 150 and display 155 of FIG. 1). The system can create a visual representation of the output if the analysis and provide it to the user. The output can be in the form of an analytical (e.g., analytical model 800 of FIG. 8) or in another form such as a chart, raw data, or other form.

Additionally the system can provide (step 1060) the analysis data for output to a dashboard (e.g., using dashboard engine 160 and display 165). The system can create a visual representation of the output if the analysis and provide it to the user. The output can be in the form of an analytical model (e.g., analytical model 800 of FIG. 8) or in another form such as a chart, raw data, or other form. Additionally the operator of the system can adjust (step 1070) system parameters based on feedback provided (e.g., using dashboard engine 160). The feedback can be used to modify the functioning of any of the components of system 100. Additionally the feedback can be used to adjust the contents of information stored in data storage (e.g., data storage 115) and the case library (e.g., case library 133).

Although the system is described in terms of a healthcare context, the system can be used for many different domains. The features used and data that is input can be based on the nuances as specifics of the domain being analyzed.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A non-transitory computer readable storage medium storing instructions that are executable by a first computing device that includes one or more processors to cause the first computing device to perform a method comprising:
   obtaining, from one or more data sources, a first set of data associated with a plurality of events;
   generating, based on at least one of the content or type of the first set of data, a second set of data;
   acquiring information associated with a target individual and one or more target events of a target event path;
   obtaining, from a case library, a third set of data associated with at least one of the plurality of events, the second set of data, of the target event path;
   determining a result associated with the target individual based on the target event path, the information associated with the target individual, and the third set of data;
   determining a first subset of one or more events of a plurality of event paths from the first set of data and the second set of data wherein the subset of one or more events have one or more common attributes with target event path;
   applying to the first subset of one or more events exclusion criteria to generate a second subset of the one or more events, wherein the exclusion criteria are based on information in the third set of data and the result; and
   generating an analytical model based on the second subset of one or more events for estimating attributes of the target event path.

2. The non-transitory computer readable storage medium of claim 1 wherein the one or more data sources are dynamically updated with new data records and wherein the method is performed in response to the dynamic update.

3. The non-transitory computer readable storage medium of claim 1, wherein the analytical model is used to estimate the cost associated with the target event path.

4. The non-transitory computer readable storage medium of claim 1, wherein generating an analytical model includes applying statistical operations to the first set of data.

5. The non-transitory computer readable storage medium of claim 4, wherein the statistical operations applied to the first set of data generate a weight value associated with each of the one or more target events.

6. The non-transitory computer readable storage medium of claim 1, wherein the analytical model is provided for output using a visual representation.

7. The non-transitory computer readable storage medium of claim 1, wherein the target individual and target event path are provided by a user.

8. An electronic device comprising:
a memory storing instructions; and
one or more processors configured to execute the instructions to cause the electronic device to perform;
obtaining, from one or more data sources, a first set of data associated with a plurality of events;
generating, based on at least one of the content or type of the first set of data, a second set of data;
acquiring information associated with a target individual and one or more target events of a target event path;
obtaining, from a case library, a third set of data associated with at least one of the plurality of events, the second set of data, of the target event path;
determining a result associated with the target individual based on the target event path, the information associated with the target individual, and the third set of data;
determining a first subset of one or more events of a plurality of event paths from the first set of data and the second set of data wherein the subset of one or more events have one or more common attributes with target event path;
applying to the first subset of one or more events exclusion criteria to generate a second subset of the one or more events, wherein the exclusion criteria are based on information in the third set of data and the result; and
generating an analytical model based on the second subset of one or more events for estimating attributes of the target event path.

9. The electronic device of claim 8, wherein the one or more data sets are dynamically updated with new data records and wherein the one or more processors configured to execute the instructions further cause the electronic device to perform obtaining, from the one or more data sources, a first set of data associated with a plurality of events.

10. The electronic device of claim 8, wherein the analytical model is used to estimate the cost associated with the target event path.

11. The electronic device of claim 8, wherein generating an analytical model includes applying statistical operations to the first set of data.

12. The electronic device of claim 11, wherein the statistical operations applied to the first set of data generate a weight value associated with each of the one or more target events.

13. The electronic device of claim 8, wherein the one or more processors configured to execute the instructions further cause the electronic device to perform presenting the analytical model using a visual representation.

14. The electronic device of claim 8, wherein the one or more processors configured to execute the instructions further cause the electronic device to perform obtaining the target individual and target event path from a user.

15. A method performed by one or more processors and comprising:
obtaining, from one or more data sources, a first set of data associated with a plurality of events;
generating, based on at least one of the content or type of the first set of data, a second set of data;
acquiring information associated with a target individual and one or more target events of a target event path;
obtaining, from a case library, a third set of data associated with at least one of the plurality of events, the second set of data, of the target event path;
determining a result associated with the target individual based on the target event path, the information associated with the target individual, and the third set of data;
determining a first subset of one or more events of a plurality of event paths from the first set of data and the second set of data wherein the subset of one or more events have one or more common attributes with target event path;
applying to the first subset of one or more events exclusion criteria to generate a second subset of the one or more events, wherein the exclusion criteria are based on information in the third set of data and the result; and
generating an analytical model based on the second subset of one or more events for estimating attributes of the target event path.

16. The method of claim 15 wherein the one or more data sources are dynamically updated with new data records and wherein the method is performed in response to the dynamic update.

17. The method of claim 15, wherein the analytical model is used to estimate the cost associated with the target event path.

18. The method of claim 15, wherein generating an analytical model includes applying statistical operations to the first set of data.

19. The method of claim 18, wherein the statistical operations applied to the first set of data generate a weight value associated with each of the one or more target events.

20. The method of claim 15, wherein the analytical model is provided for presentation using a visual representation.

* * * * *